United States Patent [19]

Toda et al.

[11] Patent Number: 4,898,654
[45] Date of Patent: Feb. 6, 1990

[54] METHOD OF PRODUCING OPTICALLY ACTIVE β-LACTAM DERIVATIVES

[75] Inventors: Fumio Toda, Ehime; Kouichi Tanaka, Matsuyama; Masatoshi Taniguchi, Suita; Michio Sasaoka, Tokushima, all of Japan

[73] Assignee: Otsuka Kagaku Kabushiki Kaisha, Osaka, Japan

[21] Appl. No.: 357,840

[22] Filed: May 26, 1989

[30] Foreign Application Priority Data

May 27, 1988 [JP] Japan .................................. 62-131263

[51] Int. Cl.$^4$ ............................................. B01J 19/08
[52] U.S. Cl. ................................................. 204/157.71
[58] Field of Search ...................... 204/157.71, 157.72, 204/157.6

[56] References Cited

U.S. PATENT DOCUMENTS 3,401,106 9/1968 Elad .............................. 204/157.71

Primary Examiner—John F. Niebling
Assistant Examiner—Ben C. Hsing
Attorney, Agent, or Firm—Armstrong, Nikaido, Marmelstein, Kobovcik & Murray

[57] ABSTRACT

Disclosed is a method of producing an optically active β-lactam derivative of the formula

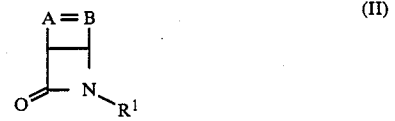

comprising irradiating with light, in solid phase, an inclusion complex of a compound of the formula

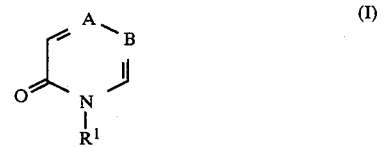

with an optically active host compound.

6 Claims, No Drawings

METHOD OF PRODUCING OPTICALLY ACTIVE β-LACTAM DERIVATIVES

This invention relates to a method of producing optically active β-lactam derivatives.

A known method of producing β-lactam derivatives of the general formula

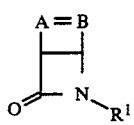
(II)

wherein A and B are the same or different and each is N, CH or C—R² in which R² is a lower alkyl group, a phenoxy group, a phenoxy group substituted with 1 to 3 lower alkoxy groups on the benzene ring or a protected hydroxy group, and R¹ is a hydrogen atom, a lower alkyl group, a phenyl group, a phenyl group substituted with 1 to 3 lower alkoxy groups on the benzene ring, a benzyl group or a benzyl group substituted with 1 to 3 lower alkoxy groups on the benzene ring, comprises irradiating a nitrogen-containing compound of the general formula

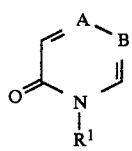
(I)

wherein A, B and R¹ are as defined above in solution with light. This method, however, gives the compound of general formula (II) only in the form of a racemic mixture.

The only method known for the production of an optically active compound of general formula (II) starting from a compound of general formula (I) comprises irradiating with light a compound of the formula (III) given below derived from a compound of general formula (I) and l-menthol, and separating the resulting mixture of diasteromers of β-lactam derivative [Tetrahedron Lett., 27, 6091 (1986)].

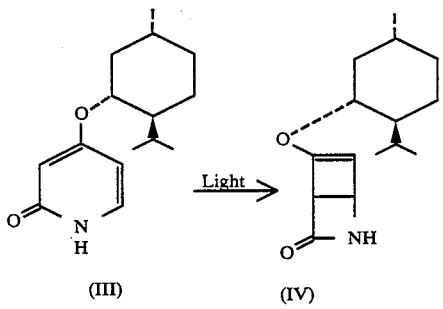

In principle, however, this method is nothing but a method of optical resolution since, even if the reaction attained a 100% conversion, only half amount of the starting material used could give the desired optically active compound. Moreover, it is known that in addition to the desired intramolecular reaction, an intermolecular reaction unavoidably proceeds to give a dimeric product. The yield of the desired optically active product cannot but be further decreased accordingly.

It is an object of the invention to provide a method of producing optically active β-lactam derivatives of the above general formula (II) selectively without causing dimer formation such as encountered in the prior art method mentioned above.

The invention thus provides a method of producing an optically active β-lactam derivative of the general formula

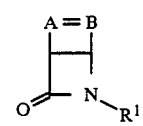
(II)

wherein A and B are the same or different and each is N, CH or C—R² in which R² is a lower alkyl group, a phenoxy group, a phenoxy group having 1 to 3 lower alkoxy groups as the substituent or a protected hydroxy group, and R¹ is a hydrogen atom, a lower alkyl group, phenyl group, a phenyl group having 1 to 3 lower alkoxy groups as the substituent, a benzyl group or a benzyl group substituted with 1 to 3 lower alkoxy groups on the benzene ring, which comprises irradiating with light, in solid phase, an inclusion complex of a nitrogen-containing compound of the general formula

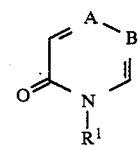
(I)

wherein A, B and R¹ are as defined above as a guest compound with an optically active host compound.

As a result of intensive investigations made by the present inventors, it was found that selective asymmetric synthesis of the desired β-lactam derivatives (II) can be realized when inclusion complexes prepared from the above-mentioned nitrogen-containing compound of general formula (I) as a guest compound and an optically active host compound are irradiated with light in solid phase without using any solvent. The present invention has been completed based on this finding.

In accordance with the invention, the optically active β-lactam derivatives of general formula (II) are produced in a selective manner and in high yields, without causing dimer formation which is inevitable in the prior art process mentioned above, by subjecting the inclusion complexes of the nitrogen-containing compound of general formula (I) as a guest compound with an optically active host compound to a solid phase photochemical reaction.

Heretofore it has never been known that the compounds of general formula (I) and optically active host compounds can form inclusion complexes and that either one of optically active isomers of the β-lactam derivative of general formula (II) can be produced selectively by irradiating the inclusion complexes in solid phase.

In this specification and in the claims, the lower alkyl group includes, among others, $C_1$–$C_4$ alkyl groups, preferably $C_1$–$C_3$ alkyl groups, such as methyl, ethyl, propyl, isopropyl, butyl and tert-butyl. The lower alkoxy group includes, among others, $C_1$–$C_4$, preferably $C_1$–$C_3$ alkoxy groups, such as methoxy, ethoxy, propoxy, isopropoxy, butoxy and tert-butoxy. The phenoxy group substituted with 1 to 3 lower alkoxy groups, in particular $C_1$–$C_4$, preferably $C_1$–$C_3$ alkoxy groups, includes, as typical examples, 4-methoxyphenoxy, 2,4-dimethoxyphenoxy, 2,4,6-trimethoxyphenoxy, 3,4-dimethoxyphenoxy, 3,4,5-trimethoxyphenoxy, 4-ethoxyphenoxy, 4-isopropoxyphenoxy and 4-tert-butoxyphenoxy. The phenyl group substituted with 1 to 3 lower alkoxy groups includes, as typical examples, phenyl groups substituted with 1 to 3 $C_1$–$C_4$ (preferably $C_1$–$C_3$) alkoxy groups, such as 4-methoxyphenyl, 2,4-dimethoxyphenyl, 2,4,6-trimethoxyphenyl, 3,4-dimethoxyphenyl, 3,4,5-trimethoxyphenyl, 4-ethoxyphenyl, 4-isopropoxyphenyl and 4-tert-butoxyphenyl. The benzyl group substituted with 1 to 3 lower alkoxy groups includes, as typical examples, benzyl groups substituted with 1 to 3 $C_1$–$C_4$ (preferably $C_1$–$C_3$) alkoxy groups, such as 4-methoxybenzyl, 2,4-dimethoxybenzyl, 2,4,6-trimethoxybenzyl, 3,4-dimethoxybenzyl, 3,4,5-trimethoxybenzyl, 4-ethoxybenzyl, 4-isopropoxybenzyl and 4-tert-butoxybenzyl. As the protective group of the protected hydroxy group, there may be mentioned, among others, those protective groups that are described by Theodora W. Green: "Protective Groups in Organic Synthesis", Chapter 2. Among such protected hydroxy groups, preferred are $C_1$–$C_4$ alkoxy groups, such as methoxy, ethoxy, propoxy, isopropoxy, butoxy and tert-butoxy; $C_1$–$C_4$ acyloxy groups which may be substituted with 1 to 3 halogen atoms, such as formyloxy, acetyloxy, chloroacetyloxy, dichloroacetyloxy, trichloroacetyloxy and trifluoroacetyloxy; $C_1$–$C_4$ alkoxycarbonyloxy groups which may be substituted with 1 to 3 halogen atoms such as methoxycarbonyloxy, ethoxycarbonyloxy and 2,2,2-trichloroethoxycarbonyloxy; benzyloxycarbonyloxy groups which may be substituted with methoxy group, such as benzyloxycarbonyloxy and p-methoxybenzyloxycarbonyloxy; and a silyloxy groups substituted with 3 substituents selected from $C_1$–$C_4$ alkyl groups and phenyl group, such as trimethylsilyloxy, t-butyldimethylsilyloxy and t-butyldiphenylsilyloxy.

Usable as the above-mentioned optically active host compound according to the invention are, for example, compounds of the formulas shown below:

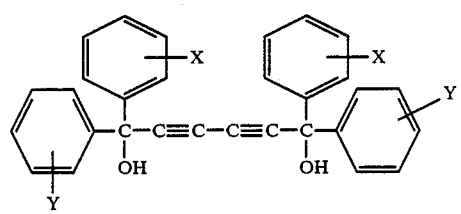
(1)

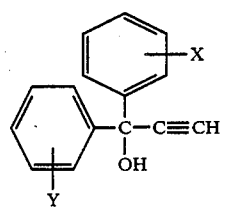
(2)

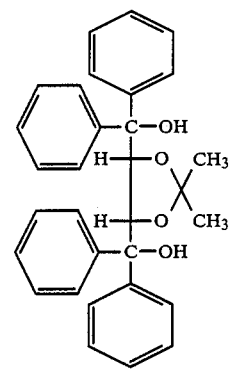
(3)

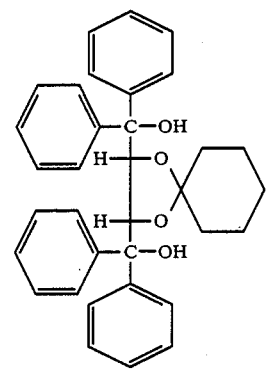
(4)

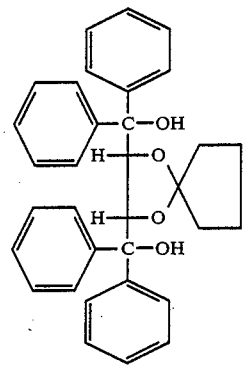
(5)

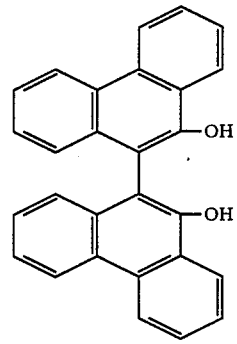
(6)

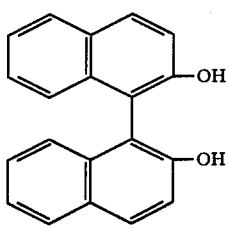

(7)

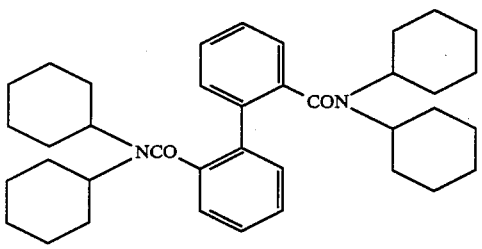

(8)

In the above formulas (1) and (2), X and Y are the same or different and each is a hydrogen atom, a methyl group or a halogen atom. The halogen atom represented by X and/or Y is, for example, a fluorine, chlorine, bromine or iodine atom.

These host compounds are either known compounds or compounds readily synthesizable by an appropriate known method.

Inclusion complexes of the above-mentioned nitrogen-containing compound (I) and optically active host compound can be readily produced by a conventional method, for example, by dissolving the nitrogen-containing compound (I) and the optically active host compound in an appropriate solvent and causing the resulting inclusion complexes to precipitate out in the form of crystals. Usable as said solvent are aromatic hydrocarbons such as benzene, toluene and chlorobenzene; lower alcohols such as methanol, ethanol, propanol and isopropanol; ketones such as acetone, methylethylketone and methylisobutylketone; lower alkyl acetate such as methyl acetate, ethyl acetate and butyl acetate; ethers such as diethyl ether, ethyl isopropyl ether, diisopropyl ether, dioxane, tetrahydrofuran and diglyme; chlorinated hydrocarbons such as methylene dichloride, chloroform, carbon tetrachloride, ethylene dichloride, trichloroethane, propylene dichloride, trichloroethylene and tetrachloroethylene; acetonitrile; aliphatic or alicyclic hydrocarbons such as pentane, hexane, cyclohexane, heptane and cycloheptane; dimethylformamide; dimethylsulfoxide; and a mixture of at least two of these solvents. The quantity ratio of the nitrogen-containing compound (I) to the optically active host compound is not particularly critical. Generally, however, the nitrogen-containing compound (I) is used in an amount of about ⅓ to 5 moles, preferably about ½ to 2 moles, per mole of the optically active host compound. The precipitation of the resulting inclusion complex in crystalline form can be effected in a conventional manner, for example, by dissolving the nitrogen-containing compound (I) and the optically active host compound with heating in a solvent such as mentioned above and allowing the resulting solution to stand at room temperature. In some instances, the inclusion complex formed may contain one or more molecules of the solvent used as included therein, and such inclusion complex may also be subjected to photochemical reaction according to the invention without causing any trouble.

In accordance with the invention, the above inclusion complex is irradiated with light in solid phase without using any solvent. The form of the inclusion complex to be treated is not critical. For efficient progress of the photochemical reaction, however, it should preferably be in the form of a powder. The source of light for irradiation is not critical provided that it can emit light of wavelengths at least partly included in the absorption wavelength range or ranges of the nitrogen-containing compound (I) to be treated, preferably light in the ultraviolet region, particularly light of the wavelength range of about 220 to 400 nm. Recommendably, the irradiation should be performed generally at a temperature of about −30° to 60° C., preferably at about 0° to 45° C. The irradiation is generally continued for a period of about 1 to 100 hours, although the irradiation time may widely vary depending on the reactor shape, the light source intensity and other factors.

The optically active β-lactam derivative (II) thus formed can be separated from the optically active host compound used by a conventional method generally known for the recovery of guest compounds from inclusion complexes, for example, by distillation under reduced pressure, column chromatography, or exchange for some other guest compound which is more susceptible to inclusion. Repeated use of the optically active host compound becomes possible by isolating the resulting optically active β-lactam derivative (II) in this manner.

Some advantageous features of the invention are as follows:

(1) Asymmetric synthesis of optically active β-lactam derivatives (II) can be achieved in high optical purity and in high yield from achiral nitrogen-containing starting compounds (I).

(2) Optically active β-lactam derivatives (II) can be produced in an economically advantageous manner since optically active host compounds can be used repeatedly.

Accordingly, the method according to the invention is a commercially very advantageous method of producing optically active β-lactam derivatives (II).

The following examples are further illustrative of the invention. In the chemical formulas given below, Ph means a phenyl group.

Example 1

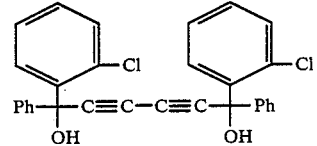

(−)-(R,R) form
Compound A

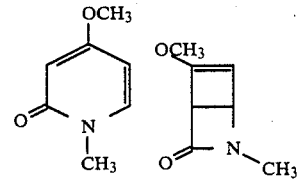

Compound B   Compound C

In 10 ml of benzene were dissolved with heating 1 g of compound A and 0.3 g of 1-methyl-4-methoxypyridone (compound B), and the solution was allowed to stand at room temperature for 6 hours. The inclusion complex of compound A with compound B precipitated out as crystals.

The inclusion complex was isolated, pulverized, and irradiated for 47 hours using a 400 W high pressure mercury lamp with Pyrex filter as the light source. After irradiation, the unreacted portion of compound B was removed by silica gel column chromatography (eluent: chloroform) and the eluate was concentrated to give the inclusion complex of compound A with compound C. The complex, which occurred as crystals, was heated at about 180° C. under reduced pressure (1 mm Hg) to give compound C as a colorless oil. Yield: 97%.

The IR spectrum of the substance thus obtained had an absorption at 1730 cm$^{-1}$ and this was in good agreement with the β-lactam structure. The specific rotation $[\alpha]_D$ (c=0.025, chloroform) of this substance was −123°. HPLC analysis using an optically active column (tradename "CHIRALCEL", product of Daicel Chemical Industries, Ltd. Japan) revealed that the optical purity of the substance was 100% within the limits of the HPLC analysis.

In 5 ml of benzene were dissolved with heating 1 g of compound D and 0.25 g of 1-methylpyridone (compound E), and the solution was allowed to stand at room temperature for 12 hours. The inclusion complex of compound D with compound E precipitated out as crystals.

The inclusion complex was isolated, pulverized, and irradiated for 45 hours using a 400 W high pressure mercury lamp with Pyrex filter as the light source. After irradiation, the irradiation product was treated in the same manner as in Example 1 to give compound F as a colorless oil. Yield: 93%.

The IR spectrum of the substance thus obtained had an absorption at 1730 cm$^{-1}$ and this was in good agreement with the β-lactam structure. The specific rotation $[\alpha]_D$(c=0.032, chloroform) was +359°. HPLC analysis using an optically active column as used in Example 1 revealed that the optical purity of the substance was 100% within the limits of the HPLC analysis.

EXAMPLE 3

The inclusion complexes of the compounds (I) shown below in Table 1 with the optically active host compounds specified in Table 1 were subjected to solid phase photochemical reaction in the same manner as in Example 1 to give the corresponding optically active β-lactam derivatives (II). The yield of these compounds (II) as well as the optical purity data obtained by HPLC analysis using an optically active column as used in Example 1 are shown in Table 2.

Example 2

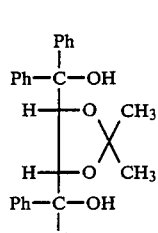
(−)-(R,R) form
Compound D

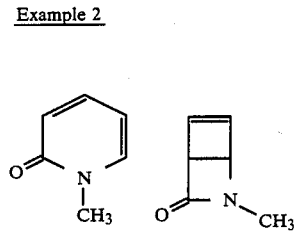
Compound E    Compound F

TABLE 1

| Run | Optically active host compound | Compound (I) | Compound (II) |
|---|---|---|---|
| 1 | Ph—C(Ph)—OH / H—O,CH₃ / H—O,CH₃ / Ph—C(Ph)—OH (−)-(R,R) form | 4-CH₃ 1-methylpyridone | CH₃ β-lactam |
| 2 | Ph—C(Ph)—OH / H—O,CH₃ / H—O,CH₃ / Ph—C(Ph)—OH (−)-(R,R) form | 4-OCH₃ 1-methylpyridone | OCH₃ β-lactam |

TABLE 1-continued

| Run | Optically active host compound | Compound (I) | Compound (II) |
|---|---|---|---|
| 3 | | | |
| 4 | | | |
| 5 | | | |

TABLE 2

| | Compound (II) | |
|---|---|---|
| Run | Yield (%) | Optical purity (%) |
| 1 | 90 | 100 |
| 2 | 88 | 100 |
| 3 | 80 | 100 |
| 4 | 68 | 100 |
| 5 | 82 | 100 |

What is claimed is:

1. A method of producing an optically active β-lactam derivative of the general formula

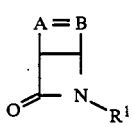
(II)

wherein A and B are the same or different and each is N, CH or C—R² in which R² is a lower alkyl group, a phenoxy group, a phenoxy group having 1 to 3 lower alkoxy groups as the substituent or a protected hydroxy group, and R¹ is a hydrogen atom, a lower alkyl group, a phenyl group, a phenyl group having 1 to 3 lower alkoxy groups as the substituent, a benzyl group or a benzyl group substituted with 1 to 3 lower alkoxy groups on the benzene ring, which comprises irradiating with light, in solid phase, an inclusion complex of a nitrogen-containing compound of the general formula

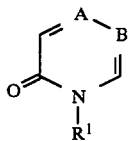
(I)

wherein A, B and R¹ are as defined above with an optically active host compound.

2. A method as claimed in claim 1, wherein the optically active host compound is a compound selected from the group consisting of compounds of the general formula

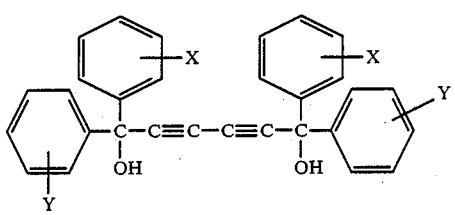
(1)

wherein X and Y are the same or different and each is a hydrogen atom, a methyl group or a halogen atom, compounds of the general formula

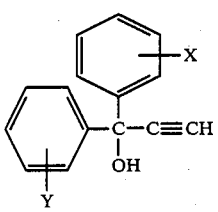
(2)

wherein X and Y are as defined above, (3)

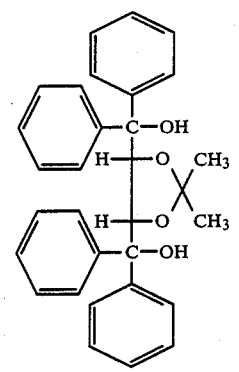

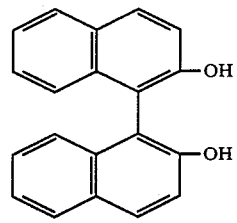

and

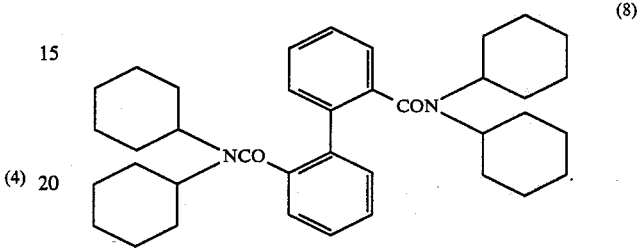

3. A method as claimed in claim 1, wherein the optically active host compound is a compound of the general formula

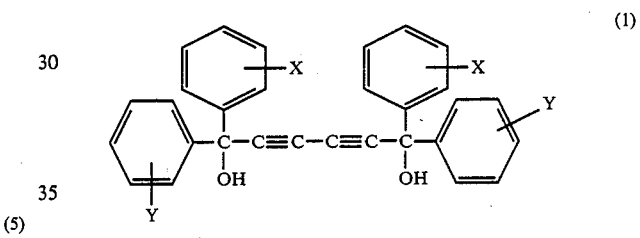

wherein X and Y are the same or different and each is a hydrogen atom, a methyl group or a halogen atom, or a compound of the formula (3)

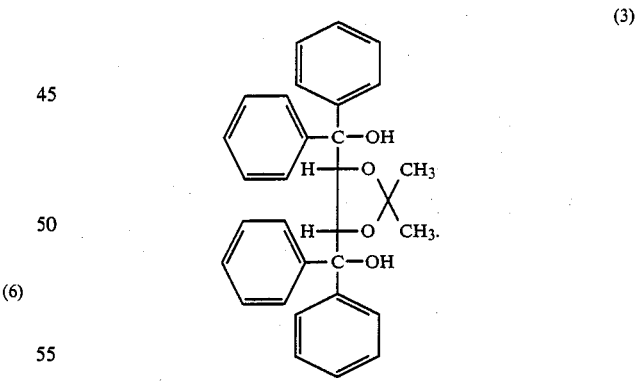

(4)

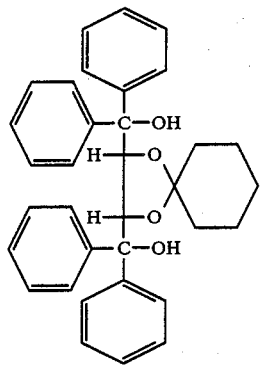

(5)

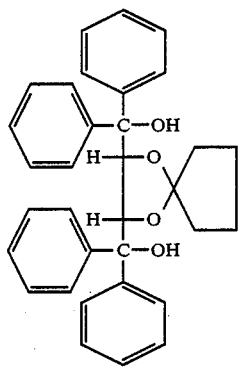

(6)

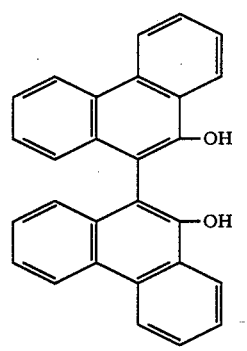

4. A method as claimed in claim 1, wherein the irradiation is performed using a light source capable of emitting light of wavelengths at least partly included in the absorption wavelength range or ranges of the nitrogen-containing compound (I).

5. A method as claimed in claim 1, wherein the irradiation is performed using light in the ultraviolet region.

6. A method as claimed in claim 1, wherein the irradiation is performed at −30° to 60° C.

* * * * *

UNITED STATES PATENT AND TRADEMARK OFFICE
CERTIFICATE OF CORRECTION

PATENT NO. : 4,898,654
DATED : February 6, 1990
INVENTOR(S) : TODA et al

It is certified that error appears in the above-identified patent and that said Letters Patent is hereby corrected as shown below:

On the cover page, Item [30], "62-131263" should read --63-131263--.

Signed and Sealed this

Twenty-first Day of May, 1991

Attest:

Attesting Officer

HARRY F. MANBECK, JR.

Commissioner of Patents and Trademarks